United States Patent [19]

Kuehnegger et al.

[11] Patent Number: 5,131,385
[45] Date of Patent: Jul. 21, 1992

[54] ORTHESIS FOR THE HUMAN KNEE

[75] Inventors: Walter Kuehnegger, Tucson, Ariz.; Hans B. Bauerfeind, Kempen, Fed. Rep. of Germany

[73] Assignee: Bauerfeind GmbH & Co., Kempen, Fed. Rep. of Germany

[21] Appl. No.: 477,997

[22] PCT Filed: Nov. 11, 1988

[86] PCT No.: PCT/DE88/00703
§ 371 Date: Jun. 21, 1990
§ 102(e) Date: Jun. 21, 1990

[87] PCT Pub. No.: WO89/04155
PCT Pub. Date: May 18, 1989

[30] Foreign Application Priority Data

Nov. 13, 1987 [DE] Fed. Rep. of Germany ....... 3738664

[51] Int. Cl.⁵ .............................................. A61F 3/00
[52] U.S. Cl. ......................................... 602/16; 602/26
[58] Field of Search ...................... 2/22, 24; 128/80 C

[56] References Cited

U.S. PATENT DOCUMENTS

| | | | |
|---|---|---|---|
| 3,911,497 | 10/1975 | Lewis, Jr. et al. | 2/24 |
| 4,241,730 | 12/1980 | Helfet | 128/80 C |
| 4,854,308 | 8/1989 | Drillio | 128/80 C |
| 4,856,501 | 8/1989 | Castillio et al. | 128/80 C |
| 4,940,044 | 7/1990 | Castillio | 128/80 C |

Primary Examiner—David Isabella
Attorney, Agent, or Firm—Owen J. Meegan; Aubrey C. Brine

[57] ABSTRACT

An orthesis for the human knee, having two joints which are disposed at the sides of the knee and from which there project arms which embrace the knee-cap and meet in pairs above and below the knee-cap in a centrally disposed tongue in each case, by each of which tongues at least one thigh strap and one leg strap respectively are carried above and below the knee. Each tongue is connected to its associated strap by an interchangeable longitudinal rail, placed in position from the outside, via adjustment means which, substantially in the region of the torque, determine the strap axis in rotation to the joints, and in the region of the strap, determine its distance from the joints.

10 Claims, 5 Drawing Sheets

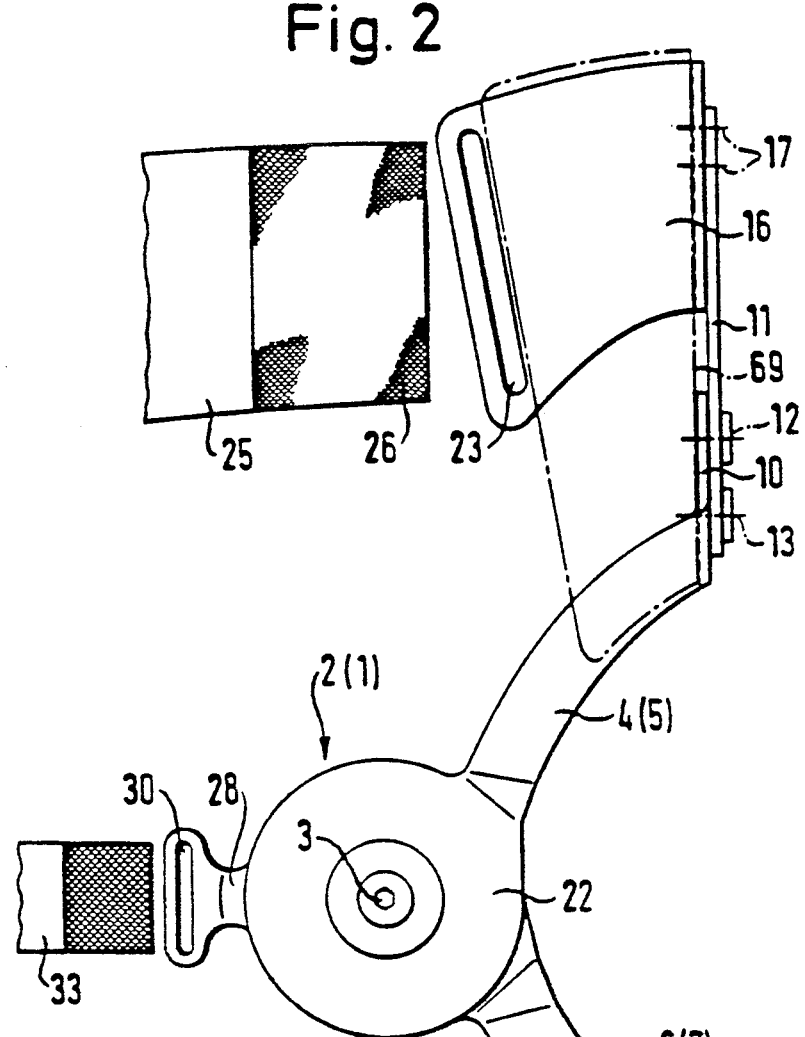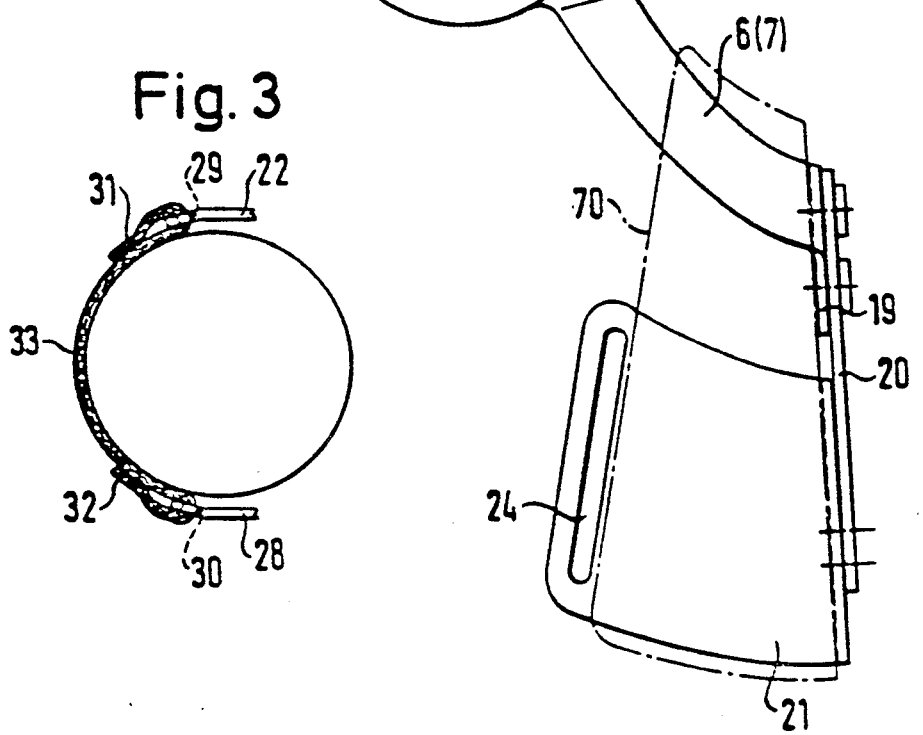

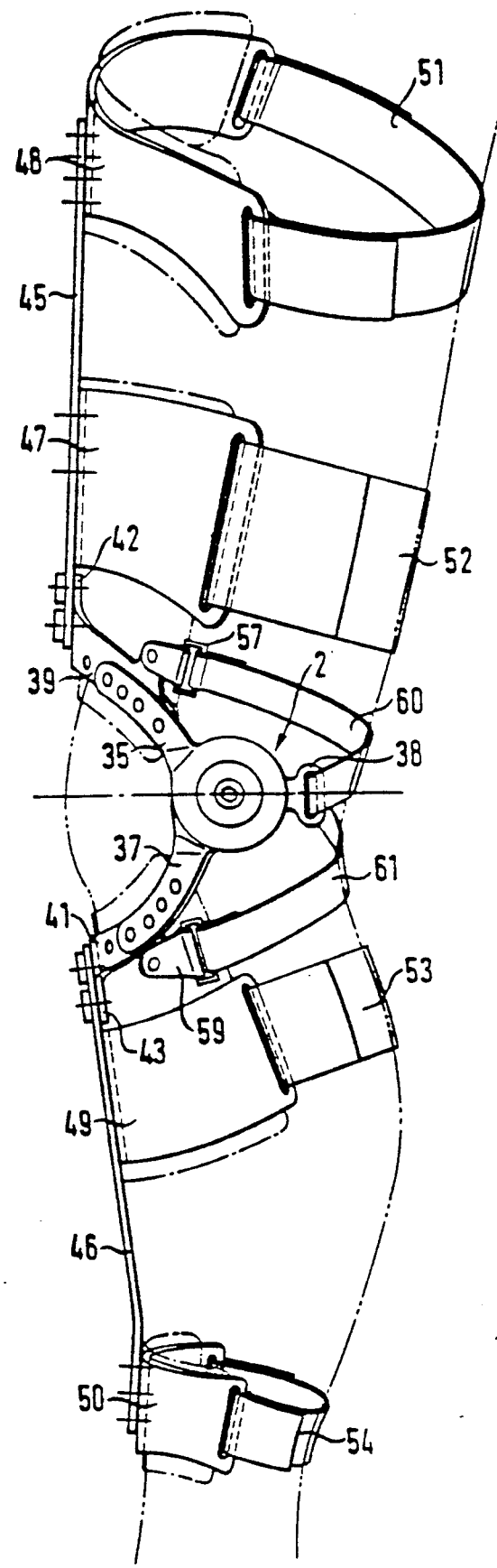
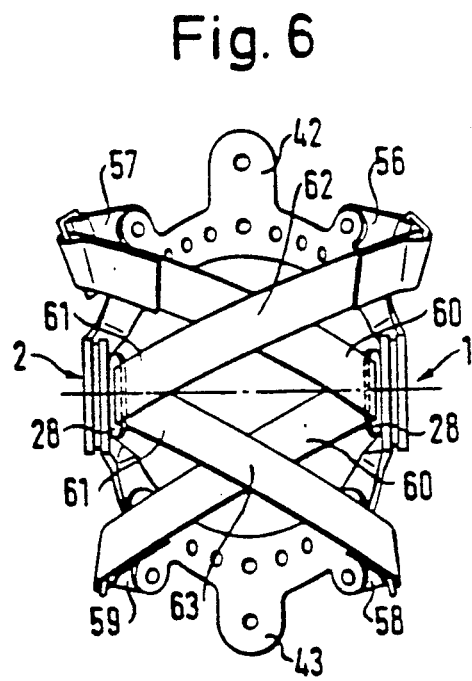
Fig. 5
Fig. 6

ORTHESIS FOR THE HUMAN KNEE

The invention relates to an orthesis for the human knee having two joints which are disposed at the sides of the knee and out of which there project arms which embrace the knee-cap and meet in pairs, above and below the knee-cap, in a centrally arranged tongue in each case, by which tongues at least one thigh strap and one leg strap are carried above and below the knee.

Such an orthesis is known. For adaptation to the leg of the particular patient, an outline drawing of the leg is prepared and then the orthesis is produced individually from this drawing or a corresponding plaster model.

It is the object of the invention to provide an orthesis which is suitable for supplying to a patient immediately and which can be largely adapted directly to the patient's leg. According to the invention, this is achieved in that each tongue is connected to its associated strap by an interchangeable longitudinal rail placed in position from the outside, via adjustment means which substantially determine, in the region of the tongue, the axis of the strap in relation to the joints and, in the region of the strap, its distance from the joints.

The orthesis thus formed renders possible its direct adaptation to the patient's leg in two ways, namely, on the one hand, by adaptation of the axis of the strap in relation to the joints of the orthesis, as a result of which the necessary right/left adjustment is effected, and in addition an adaptation to the particular longitudinal direction of the thigh or leg (O-leg or X-leg), and on the other hand an adaptation to the length of the leg by appropriate adjustment of the straps to the particular distance necessary from the joints of the orthesis. At the same time, any necessary therapeutic effects, for example the counteraction to O-leg or X-leg, are likewise achieved by suitable adjustment. The securing of the adjustment means in position in each case is effected by applying the orthesis directly to the patient's leg while the adjustment means are successive aligned and finally secured in position.

The possibility of adjusting the orthesis can be advantageously extended in that, for the purpose of adjustment in size, the tongues end in two extensions, each overlapping an arm, and are connected to the arm in question through further adjustment means which determined the length of the overlap in the longitudinal direction of the arms. As a result of the adjustment of the particular degree of overlap of extension of the tongue and arm, the following possibilities for adaptation result: By reducing the overlap, that is to say by pulling the arms out further, because the knee-cap is embraced by the arms, the two joints of the orthesis are pushed outwards so that a broader knee can be accommodated in the orthesis. In addition, in the course of this, the encompassed space is enlarged, that is to say the two tongues move away from one another so that the knee-cap is to some extent encompassed over a larger circle. At the same time there is the further effect that the position of the axis passing through the two joints can be adapted precisely to the imaginary axis of rotation of the knee joint. Finally, the particular degree of overlap can be adjusted individually, that is to say asymmetrically, so that any adaptation to axial curvature of the leg is rendered possible.

In order to render possible supporting of the thigh and leg respectively over a particularly great length, longitudinal rails of different lengths may appropriately be provided, which are provided with a plurality of adjustment means for the fitting of a plurality of straps. As a result of the use of longitudinal rails of different lengths, it is possible to secure the strap in question at an appropriate distance from the knee joint. In addition, the longitudinal rail with a plurality of adjustment means also renders possible the provision of a plurality of straps, which leads to an arrangement of straps above and/or below one another, which straps can support the leg in question over a great length according to the indication.

The straps may appropriately be made tapered, following the anatomy. The straps adjacent to the joints then open outwards and thus follow the thickening of the thigh and of the calf respectively in the direction away from the knee joint.

In order to enable the ortheses to be worn largely without any pain, they are provided at their ends with slots receiving bands and so directed that the bands lie flat against the leg. In this way, the bands are prevented from resting against the leg with only one edge for example, according to the adjustment of the strap, producing pressure points as a result and causing a disadvantageous displacement through alternating muscle pressure during movement.

The bands may appropriately be made symmetrical with self-gripping fastener supports for simultaneous tightening at both sides. This leads to an equally strong pull on the slot eyes so that the orthesis is not displaced in relation to the leg when being put on. In addition, this formation of the bands renders easy exchange possible, particularly for washing, as well as the change-over to longer or shorter bands as necessary. Either resilient material or non-extensible material may be used as material for the bands.

In order to enable the orthesis to be worn as painlessly as possible, the straps are provided with holding elements for pads of different thickness which can be inserted in the straps. The structure of the leg in question can be taken into consideration by selection of the thickness of the pads. In addition, as a result of this it becomes possible for the pads to be easily changed, which is particularly important for washing.

In order to fix the orthesis in the region of the hollow of the knee, pivotable slot eyes are provided on the two joints for bands extending in the region of the hollow of the knee. The pivotable slot eyes render possible an adaptation of the current direction of the band pulled through them to the bending of the knee.

In order to increase the comfort of wearing the orthesis and to improve it supporting at the knee, pivotable slot eyes are provided on each arm or each extension for bands extending round the hollow of the knee in such a manner that, starting from the slot eyes on the arms or extensions, a band crossing results in each case above and below the hollow of the knee, via the slot eyes at the joints. At the same time, the hollow of the knee remains free of bands but because of the way the bands are taken, a double band crossing results in which there are altogether four lengths of band extending round the knee from behind, which embrace the leg with a relatively large surface. In this manner, the hollow of the knee is not exposed to friction with the band. In this case, too, there is the possibility of using an extensible or non-extensible band material, according to the indication.

In order to avoid a possible lateral pressure on the knee joint by the joints of the orthesis, the joints of the orthesis may be appropriately be provided, at their inside, with a self-gripping fastener for the fitting of pads of different thicknesses and shapes. The orthesis can be additionally adapted to different knee widths by these pads while an individual adaptation to the particular shape of knee is possible, particularly with wedge-shaped pads.

The orthesis according to the invention is excellently suited to be assembled with its individual parts to form a construction kit so that even extreme differences in size can be taken into consideration, for example, ortheses for children or for particularly large adults. This is done by means of a construction kit which contains a collection of the individual parts of the orthesis with different sizes for assembly of the complete orthesis by means of the respective adjustment means.

Examples of embodiment of the invention are illustrated in the Figures:

FIG. 2 shows the same orthesis in side view;

FIG. 3 shows the arrangement of a band on the slot eyes provided on the joints;

FIG. 5 shows the same orthesis in side view;

FIG. 6 shows the back view of the arrangement of two bands crossing twice;

Figure 1:
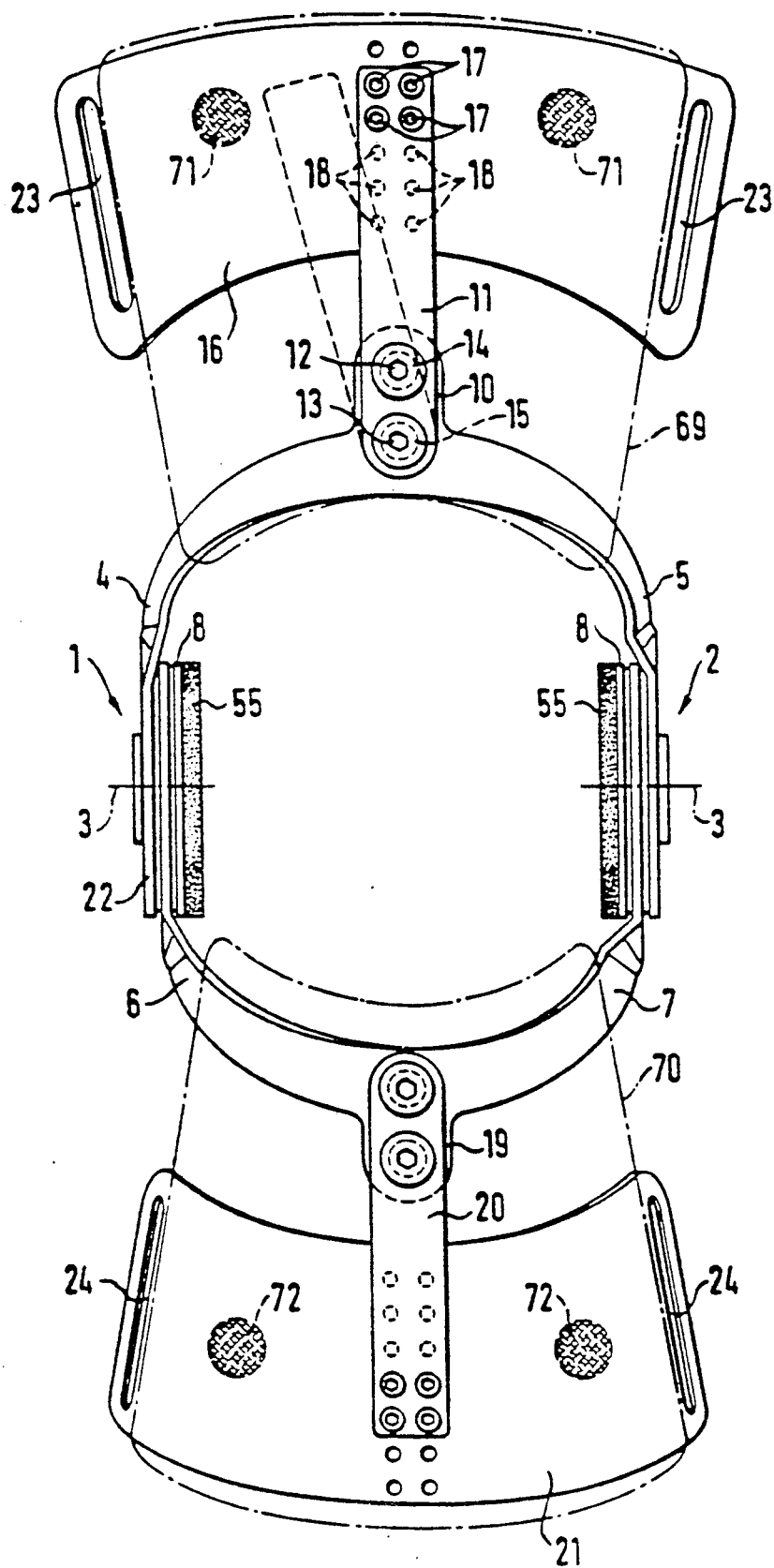
FIG. 1 shows the orthesis in front view.

The orthesis illustrated in FIG. 1 consists of the two joints 1 and 2 which are disposed at the sides of a knee and which each consist of the pin 3 screwed in at the outside, on which the arms 4 and 5 as well as 6 and 7 are pivotally mounted. This pin 3 additionally carries a disc 8 at the inside which is likewise pivotally mounted so that it is not also turned on turning of the joint 1 or 2 in relation to the enclosed knee and thus prevents friction against the knee.

The arms 4 and 5 meet in the tongue 10 which is arranged centrally in relation to the whole orthesis. The longitudinal rail 11 is secured to the tongue 10 by means of the two screws 12 and 13, while as a result of the holes 14 and 15 in the tongue 10, which are larger than the screws 12 and 13, the longitudinal rail 11 is given a possibility of adjustment in relation to the tongue 10. Thus the longitudinal rail 11 can, for example, be swung into the position shown in broken lines in relation to the tongue 10.

The strap 16 is secured to the longitudinal rail 11 by means of the four screws 17 which ensure a stable connection between the longitudinal rail 11 and the strap 16. The strap 16 is provided with two rows of holes 18 which are drilled in the strap 16 in accordance with the arrangement of the screws 17. The strap 16 can therefore be secured to the longitudinal rail 11 in positions at various distances from the joints 1 and 2 according to which holes 18 in the strap 16 are selected for the securing.

As a result of these adjustment means formed by the screws 12, 13 and 17, the strap 16 can be adapted in two respects to the patient's leg in the manner described above, namely on the one hand by displacement of the longitudinal rail 11 in relation to the tongue 10 and on the other hand by displacement of the strap 16 in relation to the longitudinal rail 11.

The arms 6 and 7 meet in the tongue 19 in the same manner. The tongue 19 is adjustably arranged and secured in relation to the longitudinal rail 20 and this is adjustably arranged and secured in relation to the strap 21 so that, with regard to this, reference may be made to the above explanation in connection with the strap 16 and the longitudinal rail 11. In the present case, the strap 16 forms a thigh strap and the strap 21 a leg strap.

The discs 8 are provided, at the inside, with a surface adapted for the clinging of a self-gripping fastener. Pressed against this surface are the pads 55 which are provided with the said self-gripping fastener at their side adjacent to the discs 8 so that the pads 55 cling to the discs 8. The pads 55 consist of plastics material and cause a gentle cushioning of the joints 1 and 2 in relation to the patient's knee enclosed by the orthesis. The pads are available in different thicknesses and different shapes so that they can be used to suit the knee of the patient in question as required.

In FIG. 2, the same orthesis is illustrated in side view. As shown, the arm 4 is made integral with the plate 22 which is pivotally carried by the pin 3 and rests flat against corresponding plates of the arms 5, 6 and 7. As a result of this plate-shaped construction, known per se, of the relevant parts of the joints 1 and 2, the stability of their connection is guaranteed.

In FIGS. 1 and 2, also provided at the ends of each of the straps 16 and 21 are the slots 23 and 24 which each extend obliquely to the longitudinal direction of the thigh or lower leg respectively so that bands pulled through the slots can lie flat against the leg. The bands are each provided at their two ends with a self-gripping fastener so that they can be pulled tight and fixed at both sides of the straps 16 and 21. In FIG. 2, the band 25 is illustrated in connection with the strap 16 and its region 26 provided with the self-gripping fastener is indicated by cross-hatching.

The arrangement for securing the band 25 will be explained in connection with FIG. 3. FIG. 3 shows, as a detail, the two slot eyes 27 and 28 (slot eye 28 see FIG. 2), which are pivotally mounted on the joints 1 and 2. The ends 31 and 32 of the band 33 are each threaded through the slots 29 and 30 respectively of the slot eyes 27 and 28 and folded over towards the portion of the band 33 situated between the slots 29 and 30 so that the ends 31 and 32 are firmly held on the band 33 by means of self-gripping fastening. This method of securing and arranging a band is also provided for the bands pulled through the slots 23 and 24 respectively (see band 25 according to FIG. 2).

It can clearly be seen from FIG. 3 that as a result of simultaneous and uniform pulling on the ends 31 and 32 of the band 33, the band 33 is uniformly tightened without the orthesis being displaced in relation to the leg. In the orthesis illustrated in FIGS. 1 and 2, the band 33 extends over the knee joint and as a result permits a precise adjustment for the accordance of the two joints with the anatomical knee joint.

The straps 16 and 21 are backed by removable pads 69 and 70 which consist of foamed material and so protect the leg of the wearer of the orthesis from pressure. The two pads 69 and 70 are shown in FIGS. 1 and 2 by outlining in chain line. The pads extend from the straps 16 and 21 to beyond the associated arms 4, 5 and 6, 7 respectively so that a far-reaching cushioning results under the longitudinal rails 11 and 20 as well. In order to enable the pads 69 and 70 to be removed, the straps 16 and 21 are provided at the positions 71 and 72 shown cross-hatched with a self-gripping fastener surface which clings to the corresponding surfaces of the pads 69 and 70.

Figure 4:
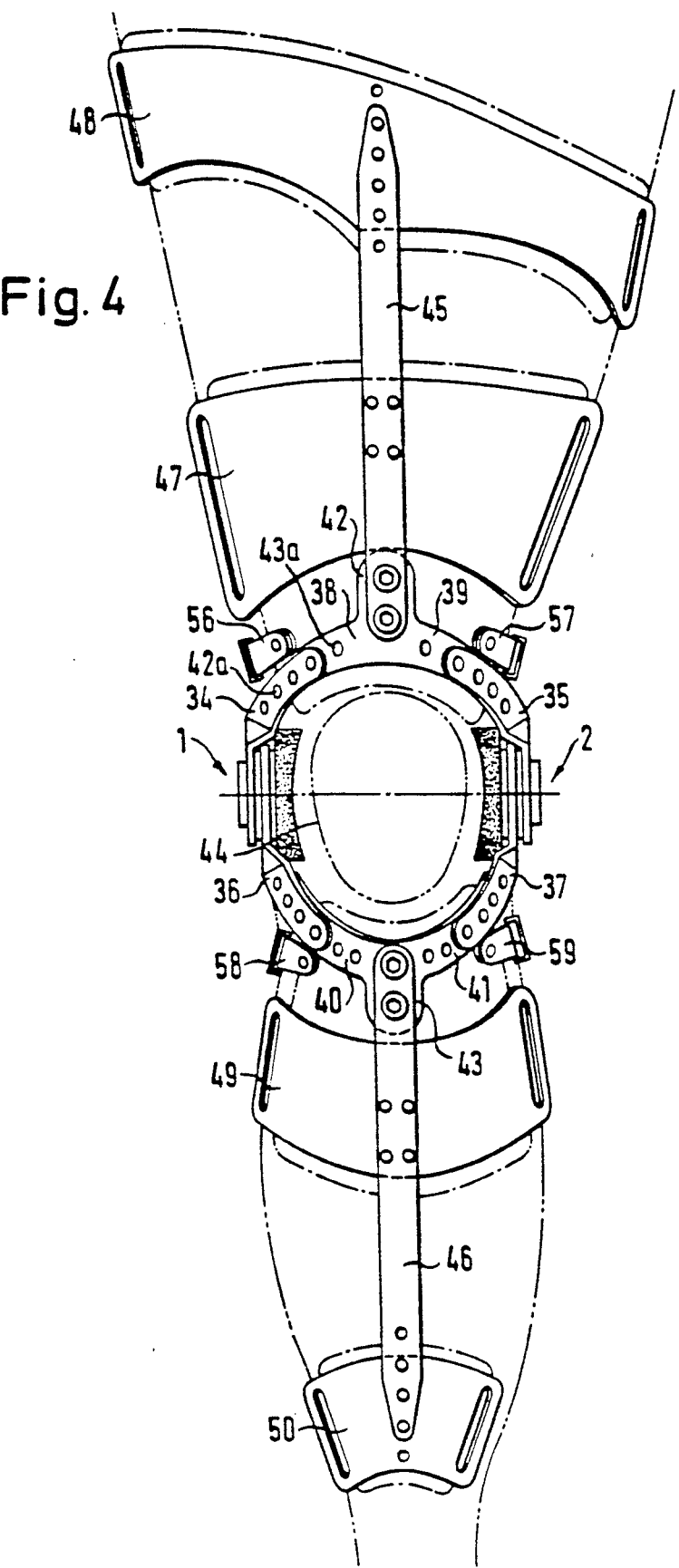
FIG. 4 shows the front view of an orthesis with a plurality of straps at each side of the knee and with adjustment means in the region of the arms and of the extensions of the tongues.

An orthesis which is additionally provided with an adjustability in size effective in the region of the knee joint will now be described with reference to FIGS. 4 and 5. FIG. 4 shows the orthesis fitted to a leg in front view and FIG. 5 shows the same orthesis in side view.

Like that shown in FIGS. 1 and 2, the orthesis comprises the two joints 1 and 2 from which the arms 34 and 35 as well as 36 and 37 project. The arms 34 and 35 or 36 and 37 respectively overlap lateral extensions 38,39 and 40,41 respectively which are components of the two tongues 42 and 43. The arms 34, 35 and 36, 37 as well as the extensions 38, 39 and 40, 41 are provided with holes 42a and 43a respectively which serve as adjustment means and render possible the fixing of the arms to the extensions with a different length of overlap in each case. For this purpose, screws are inserted in the holes 42, 43, as a result of which the mutual fixing of the arms to the extensions is brought about. The holes 42 in the arms and the holes 43 in the extensions each have the same spacing in relation to one another so that the particular overlap can be adjusted step by step over a relatively wide range. With little overlap, the arms 34, 35 and 36, 37 together with the extensions 38, 39 and 40, 41 form a relatively large circle round the knee-cap illustrated in chain line, since the distance of the tongues 42 and 43 from the axis of the two joints 1 and 2, which axis is shown as a straight chain line, is relatively great. In addition, with little overlap, there is a correspondingly great distance between the two joints 1 and 2. Conversely, with much overlap, correspondingly reversed conditions are naturally obtained. In addition, it is possible to adjust each overlap individually, that is to say, in particular, asymmetrically, as a result of which, as already explained above, any individual necessary adaptation to the leg of the patient in question can be rendered possible.

Screwed to the tongues 42 and 43 in the same manner as described in connection with FIGS. 1 and 2 are the longitudinal rails 45 and 46 which here each carry two straps, namely on the one hand the straps 47, 48 and 49, 50. The securing the these straps to the longitudinal rails 45 and 46 is effected in the same manner as described with reference to FIGS. 1 and 2.

From FIG. 5, it is clear that as a result of the position of the slots in the ends of the straps 47, 48, 49 and 50, the bands threaded through in each case lie flat against the patient's leg so that tilting of the bands 51, 52, 53, 54 in relation to the leg is impossible.

The orthesis illustrated in FIGS. 4 and 5 further comprises separate components for the fitting of two bands in the region of the hollow of the knee. Apart from the slot eyes 28 (see also FIG. 2), there are the slot eyes 56 and 57 as well as 58 and 59. All these slot eyes are pivotally mounted so that they can adapt their direction to the pull of the bands secured to them. As can be seen in particular from FIG. 6, two bands 60 and 61 are provided which are taken in such a manner that a band crossing 62 or 63 respectively occurs in each case above and below the hollow of the knee. The band 60 is taken from the slot eye 57 to the slot eye 28 on the joint 1 and from here to the slot eye 59. The band 61 runs from the slot eye 56 to the slot eye 28 on the bearing 2 and then to the slot eye 59. As can be seen from FIG. 6, the two band crossings 62 and 63 are formed in the course of this, between which the hollow of the knee lies free thus preventing chafing by the bands 60 and 61 on movement of the knee.

In FIGS. 4 and 5, the arrangement of pads behind the straps 48, 47, 49 and 50 is illustrated, corresponding to the illustration in FIGS. 1 and 2, namely by outlining in chain line. These pads are fitted to the straps by means of self-gripping fasteners in the same manner as described with reference to FIG. 1.

Figure 7:
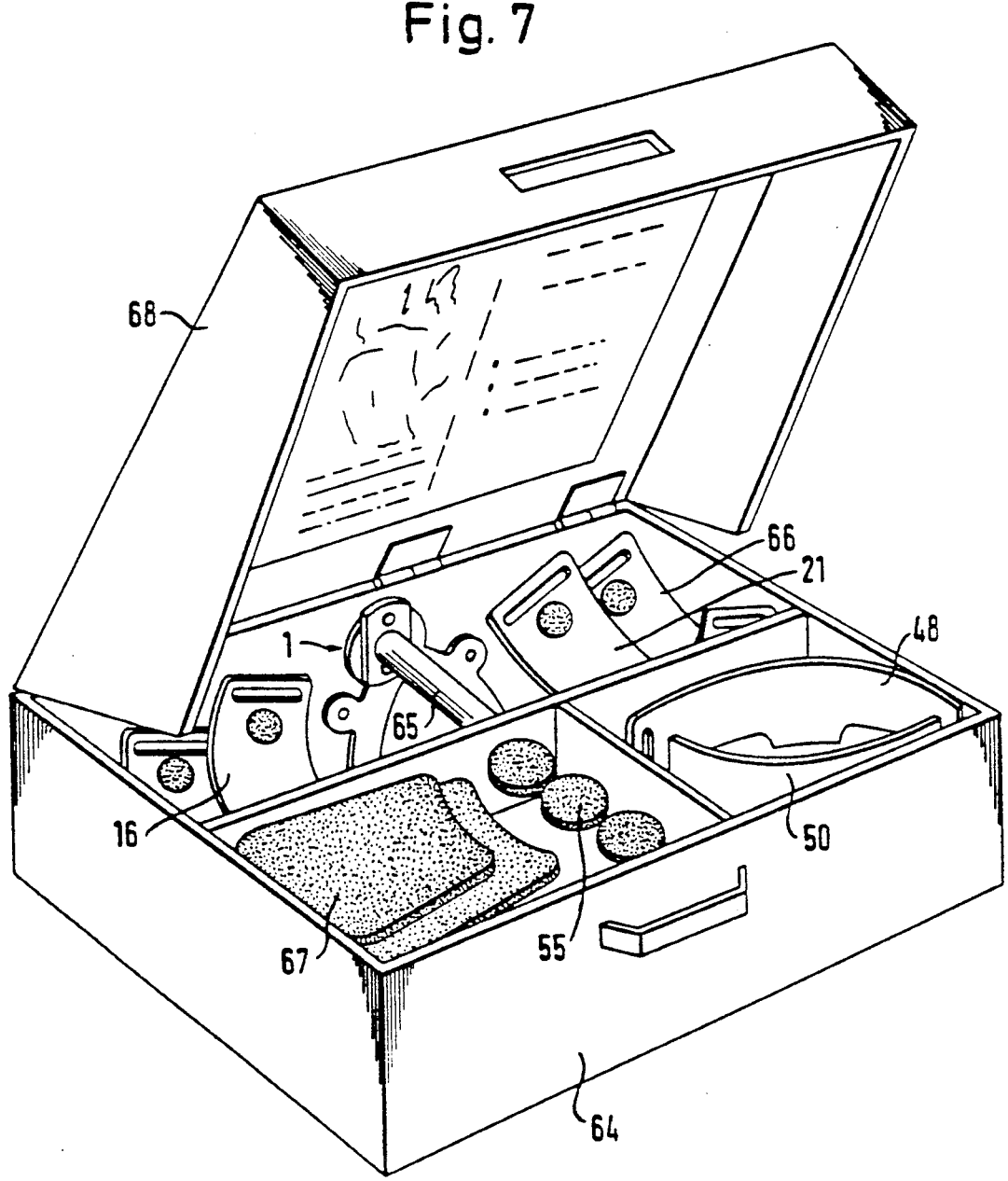
FIG. 7 shows a construction kit for assembling the orthesis.

In FIG. 7, a construction kit 64 is illustrated which contains a collection of the individual parts of the orthesis shown in FIGS. 1 and 2 in various sizes. Assembled in the construction kit there can be seen this orthesis with its straps 16 and 21, with the parallel alignment device 65 disposed between the joints (only the joint 1 is visible). The construction kit 64 contains, inter alia, the further strap 66 of a different size, in addition to pads 67 and the pads 55 which can be fitted to the joints. Furthermore, the outer straps 48 and 50 visible in FIGS. 4 and 5 are stored in the construction kit. In this manner, all the individual parts with respective adjustment means which also serve for the joining together are accommodated in the construction kit so that any patient can be dealt with by being supplied immediately from the construction kit 64. Drawings and instructions for the assembly of the orthesis are provided at the inside of the cover 68 of the construction kit 64.

We claim:

1. An orthesis brace for the human knee comprising two rotatable joints defining a rotational axis and which are disposed at the medial and lateral sides of the knee, said joints having proximal and distal arms extending therefrom, said arms being configured to embrace the kneecap and including a centrally disposed tongue extending outwardly proximally and distally from said proximal and distal arms, respectively, along the front of the leg;

each of said tongues carrying at least one thigh strap and one leg strap above and below the knee; and
   an adjustment means connecting said tongue to said at least one thigh and leg straps, respectively by an interchangeable longitudinal rail, said adjustment means providing for angular adjustment of the longitudinal rail and the respective strap in relation to the rotational axis of the joints, said longitudinal rail further including means for adjusting the distance of the strap from the joints.

2. An orthesis according to claim 1 further characterized in that the tongues end in extensions each overlapping an arm and which are connected to a respective arm by other adjustment means for determining the length of the overlap in the longitudinal direction of the arms to thereby provide for adjustment in size thereof.

3. An orthesis according to claims 1 or 2 further characterized in that the longitudinal rails are of different length and each is provided with a plurality of adjustment means for fitting a plurality of straps thereto.

4. An orthesis to claims 1 or 2 further characterized in that the straps adjacent to the joints are tapered to thereby follow the anatomy of a user.

5. An orthesis according to claims 1 or 2 further characterized in that the straps are provided at their ends with slots receiving bands therein, the slots being disposed in a direction such that the bands lie flat against the leg of a user.

6. An orthesis according to claim 5 characterized in that the bands are symmetrically constructed with a self-gripping fastener support at each end thereof for simultaneously tightening the bands at both sides of the leg of the user.

7. An orthesis according to claims 1 or 2 characterized in that the straps are provided with holding elements for attachment of pads of different thickness which may be attached to the straps.

8. An orthesis according to claims 1 or 15 characterized in that pivotal slot eyes are provided on both the joints for receiving bands extending in the region of the hollow of the knee of the user.

9. An orthesis according to claim 8 characterized in that the pivotal slot eyes are provided on each arm or on each extension for receiving bands extending around the hollow of the knee in such a manner that starting from the slot eyes on the arms or extensions, a crossing of the band results above and below the hollow of the knee in each case, with the band extending through the slot eyes on the joints.

10. An orthesis according to claims 1 or 15 characterized in that the joints are provided at their inside with a self-gripping fastener for attachment of pads or different thicknesses and shapes.

* * * * *